United States Patent
Saleh (10) Patent No.: US 8,556,883 B2
(45) Date of Patent: Oct. 15, 2013

(54) MEDICAL SURGICAL NAVIGATION SENSOR MOUNTING SYSTEM

(76) Inventor: Rafic Saleh, Aguadilla, PR (US)

( * ) Notice: Subject to any disclaimer, the term of this patent is extended or adjusted under 35 U.S.C. 154(b) by 0 days.

(21) Appl. No.: 13/406,243

(22) Filed: Feb. 27, 2012

(65) Prior Publication Data

US 2013/0225962 A1    Aug. 29, 2013

(51) Int. Cl.
*A61M 25/098* (2006.01)

(52) U.S. Cl.
USPC .......................................................... 604/529

(58) Field of Classification Search
USPC .......................................................... 604/529
See application file for complete search history.

(56) References Cited

U.S. PATENT DOCUMENTS

| | | | |
|---|---|---|---|
| 8,207,446 B2 * | 6/2012 | Swift et al. ................. | 174/110 R |
| 2005/0255317 A1 * | 11/2005 | Bavaro et al. ................. | 428/375 |
| 2006/0004286 A1 * | 1/2006 | Chang et al. ................... | 600/435 |
| 2008/0161774 A1 * | 7/2008 | Hastings et al. .............. | 604/524 |
| 2009/0005733 A1 * | 1/2009 | Chiu et al. ................... | 604/99.01 |
| 2010/0228112 A1 * | 9/2010 | Von Malmborg ............. | 600/373 |
| 2011/0066029 A1 * | 3/2011 | Lyu et al. ...................... | 600/424 |
| 2011/0137155 A1 * | 6/2011 | Weber et al. .................. | 600/424 |
| 2011/0152721 A1 * | 6/2011 | Sela et al. ..................... | 600/585 |
| 2012/0130218 A1 * | 5/2012 | Kauphusman et al. ........ | 600/373 |

* cited by examiner

*Primary Examiner* — Aarti B Berdichevsky
(74) *Attorney, Agent, or Firm* — Donn K. Harms (57) ABSTRACT

An engagement system for a surgical sensor assembly, formed of a sensing component in a fixed position and a lead wire in an electrical communication therewith. The engagement system employs a jacket of heat shrink polymeric material to hold the sensing component to the lead wire and eliminates the employment of soldering and welding and crimping which can damage such sensing components. The system is employed in combination with catheters having a lumen for control wires for surgical instruments.

19 Claims, 7 Drawing Sheets

MEDICAL SURGICAL NAVIGATION SENSOR MOUNTING SYSTEM

BACKGROUND OF THE INVENTION

1. Field of the Invention

The present invention relates to surgical devices employed for minimally invasive surgery. More specifically the invention relates to a sensor mounting device and system which provides secured non-damaging electronically communicative engagement of a medical sensor to a lead wire and surgical instrument. The invention is most suitably adapted for engagement with needles, guide wires, catheters, cytology brushes, biopsy forceps, and other devices employed using electronic navigation to determine positioning in the body of a patient.

2. Prior Art

The medical industry is a field which is constantly seeing technological changes, advancements, and improvements. Minimally invasive surgery and computer assisted surgery (CAS) is a recent development which allows physicians to perform procedures with the aid of computer technology which provides a means to visually determine instrument positioning in the body of a patient. Such CAS systems are a promising factor in the development of new robotic surgery and improvement of old minimally invasive methods. CAS is also known as computer aided surgery, computer assisted intervention, image guided surgery, and surgical navigation.

An important component of CAS is the development and construction of an accurate model of the patient with an exceptionally accurate means to determine instrument positioning using the acquired or determined patient model. Medical imaging methods which produce such models include CT scans, MRI, x-rays, and ultrasound to name a few. It is a goal of such imaging methods to produce a 3D data set which ultimately yields a virtual image of the patient's soft and hard tissues. This virtual patient model when employed with a patient in position registered to the model, can be referenced during the actual surgery upon the patient to help the surgeon guide instruments, take tissue samples, and perform other surgical procedures. Matching a patient virtual model to the actual patient is often referred to as patient registration.

The actual patient intervention in CAS occurs as surgical navigation. Here, a surgeon and a computer controlled surgical robot, or the surgeon, must correlate their procedural actions. In general, the surgical robot is preprogrammed to carry out certain tasks during preoperative procedures. Robot surgery can conventionally be divided to three types, namely, supervisory-control, telesurgical, and shared-control. In the former, the robot solely performs the tasks via pre-programmed actions.

In telesurgical type systems, a surgeon remotely operates controls to manipulate robotic arms, this type is also called remote surgery. The latter is similar to remote surgery, however, the robot can be programmed to steady the instruments during manipulation by the surgeon. As can be imagined, the desired mode of surgery will vary from case to case depending on complexities and the particular case at hand.

Additional surgical procedures, using virtual models and patient registration for navigation, are performed by the surgeons themselves, frequently using their deft surgical skills. During such procedures the surgeon employs the virtual model and patient in a registered position to determine the exact position of a surgical instrument being controlled by the surgeon. Such a procedure includes for instance, tissue sampling in the lungs, where it is very important to sample tissue from particular positions in the lung. Using surgical navigation systems, the surgeon can ascertain exact positioning during the tissue sampling and obtain samples from deep within the lung.

For nearly all types discussed above, during the operation, it is necessary to correctly navigate the surgical instruments being employed during a procedure. Common surgical instruments include, needles, guidewires, stents, filters, occluders, retrieval devices, leads, catheters, cytology brushes, biopsy forceps, as well as others. Navigation and monitoring of the exact positioning in the patient's body of such surgical instruments is accomplished by the employment of tracking instrument reference markers, as well as non-tissue internal and external reference markers or sensors. Often the instrument reference marker is tracked in real time and relayed to a visual output, such as a computer screen, showing the location of the instrument within a virtual patient image. In the case where tracking is accomplished via electromagnetic systems, the markers are coils to which must be communicated an induced voltage to broadcast their position. Using multiple detectors in multiple positions, the coil position can be monitored extremely accurately and virtually positioned to coordinate positions within the virtual image. Thus, an extremely accurate image guided surgical navigation is provided.

One typical problem encountered with image guided surgical navigation however, is the physical mounting of the electromagnetic (EM) markers (herein the terms 'EM marker', 'marker', 'EM sensor', and 'sensor' may be used interchangeably and refer to any such marker or sensors deemed suitable for the intended purpose of image guided surgical navigation) to the surgical instruments themselves. As one could imagine, the precision and accuracy needed during surgical procedures requires sensors which are extremely small and extremely sensitive which renders them extremely fragile.

Conventionally, it is required to engage the marker or sensor to the tip or distal end of a lead wire providing current to the marker, as well as the surgical instrument. Additionally the sensor must be maintained in a dry condition and accurately positioned on the surgical instrument being employed, which only adds to the difficulty of such a mounting.

Current conventional mounting techniques for engaging small EM sensors to lead and power wires, include soldering, crimping, and adhesives. However, in reference to the problems discussed above, and with further development of even more sensitive and fragile sensors, the conventional mounting methods simply fall short. Using conventional methods of mounting, the electrical connection between the sensing element and electrical lead wire frequently disengages or becomes damaged. Further, using heat of soldering or welding, or crimping, to engage the small and fragile EM sensor to a lead wire is frequently damaging to both the sensor and the connection yielded.

If the sensor or electrical connection is advertently damaged, at this point during manufacture, it can cause the electrical connection to be disturbed or destroyed. If this happens and is found during quality control, the device is determined useless and the valuable part, with many man hours invested to form it, is wasted. This drives up costs for the manufacturer as well as medical customers. Should the poor or failing connection get past quality control and fail during surgery, the tracking and therefor navigation will be incorrect and is unacceptable. Worse, failure or mis-information as to location can endanger the patient.

As such, there is a continuing unmet need for an improved EM sensor mounting system for medical instruments employing fragile small sensors engaged to lead wires communicating with a surgical instrument, as needed for surgical navigation. The device and method should be employable for all types of sensors and marker used in the art of surgical navigation, but especially for EM type devices which depend upon a radiated pattern of transmission for accuracy. Such a device and method should advantageously provide improved mounting means for a plurality of medical instruments without damaging the sensor, marker, or lead wires while concurrently providing an insulated cover to protect from abrasion and moisture.

SUMMARY OF THE INVENTION

The device herein disclosed and described provides a solution to the shortcomings in prior art and achieves the above noted goals. This is accomplished through the provision of a medical sensor mounting device and system especially well adapted for employment with the small fragile sensors using induced current for position tracking and which must be accurately registered in engagement with surgical navigation instruments. The improved mounting system is employable for many surgical systems commercially available and will encourage wider deployment of such systems by assuring undamaged sensor devices upon completion of manufacture.

Because of their small size and delicate nature of the wire-wrapped EM sensor components, and similar delicate electronic devices, problems have arisen in their manufacturing and their engagement to surgical devices resulting in a higher than preferred failure rate during manufacturing which drives up costs. This and similar such medical sensors requiring high precision, are extremely fragile. Consequently, while maintaining a secured electrical connection to a lead wire is a must, conventional engagement methods noted above frequently result in a destroyed sensor during manufacture. Even if not damaged during manufacturing, current mounting techniques frequently result in a poorly constructed sensor due to damage to delicate windings or to wire engagements which may fail during use.

Employing the sensor and wire engagement system herein, independently or in combination as a concurrent means for instrument engagement, the yielded sensors are especially well adapted to yield high quality navigation positioning for surgical instruments used with virtual patient models. Using the system for engagement herein, the engaged sensor and lead wire may easily be engaged to surgical instruments. Such instruments are any from a group including but not limited to needles, guide wires, stents, filters, occluders, retrieval devices, leads, catheters, cytology brushes, biopsy forceps, as well as other instruments where location tip tracking or sensing is desired. In all modes of the disclosed device and method herein, there is formed at least one movement-restrictive insulated axial pathway in which the sensor, including sensing component and electrical wires, are securely engaged in electrical and communication through positioning therein.

In a first particularly preferred mode, the sensor, including sensing component and lead electrical wire, is mountable or otherwise engaged directly to the exterior or interior of the lumen-engaged instrument within its own formed insulated axial pathway. It is preferred that the pathway is a jacket surrounding the formed sensor which is formed via a polymeric shrink wrap or a shrink tube engaged over the sensor and lead wire through thermoforming or positioning a tubular structure thereon.

Employing polymeric material formed as a tube adapted to shrink, or in a sheet adapted to thermoform around the formed sensor device, the sensing component may be electrically engaged to the lead wire, without the employment of solder, heating, crimping, welding or other methods which have proved unreliable and destructive. This provides a much more reliable manner to manufacture the sensors with much less chance of damage thereto during the process.

During thermoforming or heating, the polymeric material will form a tube or jacket about the already electrically engaged sensor and instrument. The resulting engagement of the shrunken polymeric material about the circumference of the engaged wire and sensing component will provide a slight to moderate compressive force thereto, along the aggregate length of both of the assembled components. This force as well as any adhesive aspect of the polymeric material, provides a means to maintain both the sensing component and lead wire, in their pre-positioned electrical communicative engagement. The formed engagement thereafter ensures the electrical connection between the sensing component and lead electrical wire is maintained during shipping, storage, and eventually its use within the body of a patient.

The method and structure provides an advantage over conventional mounting techniques, such as adhesives, or solder, or welding, or crimping. Such conventional methods and apperatuses use mechanical or other methods to join the sensing component to the lead wire and frequently destroy or yield an unreliable resulting device.

Heat shrinking material forming the jacket is formed of polymeric material such as a thermoplastic material such as polyolefin, fluoropolymer (such as FEP, PTFE or Kynar), PVC, neoprene, silicone elastomer or Viton. Depending on the material to be employed, there are generally two ways that heat shrink polymeric material may work. If the polymeric material contains many monomers, then when the tubing is heated the monomers polymerise. This increases the density of the material as the monomers become bonded together, therefore taking up less space. Accordingly, the volume of the material shrinks when heated.

Heat shrink can also be expansion-based. This process involves employing polymeric tubing as normal, heating it to just above the polymer's crystalline melting point, and mechanically stretching the tubing (often by inflating it with a gas). Such polymeric material is then rapidly cooled. Later, when heated, the polymeric material or tubing will relax back to its original un-expanded size. In either manner, the polymeric material employed herein, will be configured by those skilled in the art, to operatively shrink to the desired length and diameter when heated to hold the sensor component, operatively engaged to a lead wire.

Thus, the polymeric material forming the shrink wrap or shrink tube or polymeric jacket surrounding the assembled assembly of lead wire and sensing component may be any material known in the art suitable for the intended purpose including such as but not limited to any one or a combination of polymeric materials, from a group including polyester, polyolefin, flouropolymers, polyurethene, polyvinyl chloride and polyester, polyethylene terephthalate, PVC, neoprene, and silicone elastomer. Other polymeric materials adapted to shrink when heated to yield a fixed length and compressive engagement jacket as would occur to those skilled in the art are also considered included herein. The material may be picked or mixed to yield a desired compressive force when heated to shrink at rates well known in the art. Additionally, the heat shrink material, formed to heat shrink tubing, may contain a layer of thermoplastic adhesive on the inside to help provide a good seal and better adhesion. Also, adhesion may provided by the compressive friction from the closely conforming materials. Heating plain, non-adhesive shrink tube to very near the melting point, may allow it to fuse to the underlying material as well.

The use of the heat shrink material herein, can be with or without a thermoplastic adhesive layer depending upon whether the heat shrink material is to surround just the sensor assembly, or the sensor assembly and a catheter surface, or a control wire surface. In some cases the thermoplastic layer will be included to increase adhesion, and in others such as with the catheter surface, heating to a bond will provide the desired adhesion.

In yet other modes of the device, the formed sensor of lead wire and sensing component, may be mounted concurrently, or subsequently, using the heat or thermoforming process to place the formed component adjacent to the surgical instrument operated using single or multiple lumen catheters. For example, for use with an aspiration needle, the needle control wire communicates through the larger of two lumens of a catheter. Using the system herein, the sensor may be engaged within, and held in electrical communication with its lead wire within a second lumen which runs parallel to the larger lumen. As such, the sensor can be engaged within the lumen in operative position to track the distal end of the employed catheter or aspiration needle while concurrently being isolated from the needle and control wire. In this mode of sensing component and lead wire engagement, the sensor can be maintained in an insulated pathway of one lumen and the catheter simply employed during the surgery using the desired instrument.

In another preferred mode of registered engagement, the second lumen of the multi-lumen catheter can be formed or sized equal to or slightly shorter than the aggregate length of the engaged sensing component and lead wire. In this fashion the sensing component remains electrically engaged to the lead wires by a biased compressive forced of the shorter and narrow lumen. This mode of jacket formation insures the electrical connection of the sensing component to the lead wire is maintained, while still avoiding the destructive and damaging conventional manner for such engagements.

Other modes of the device, which employ multi or single lumen catheters and a polymeric jacket or tube material are discussed shortly below. In all modes shown, the delicate sensing component is held in electrical communication on the distal end of a lead wire, without employing potentially destructive mechanical or heated engagements there between.

With respect to the above description, before explaining at least one preferred embodiment of the herein disclosed invention in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other structures, methods and systems for carrying out the several purposes of the present disclosed device in the mounting and maintaining of operational electrical coupling between a sensing component and lead wire while engaged to a lumen device such as a catheter. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and mayor may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and mayor may not be present depending upon whether or not they affect the activity or action of the listed elements. Further the word "catheter" or "tube" indicates any elongated device providing one or a plurality of lumens for the operation of a surgical instrument therethrough and should in no manner be considered limiting.

It is an object of the invention to provide means to maintain the electrical communication between a sensing component and its electrical lead wire, without the need to employ conventional destructive methods of soldering and crimping and the like.

It is a further object of this invention to provide such an engaged sensing component and lead wires to, form or provide an operative communication with, a lumen bearing device adapted for operating a surgical instrument.

These together with other objects and advantages which become subsequently apparent to those skilled in the art on reading this specification, reside in the details of the construction and operation as herein described with reference being had to the accompanying drawings forming a non-limiting part thereof, wherein like numerals refer to like parts throughout.

DETAILED DESCRIPTION OF THE PREFERRED EMBODIMENTS OF THE INVENTION

Figure 1:
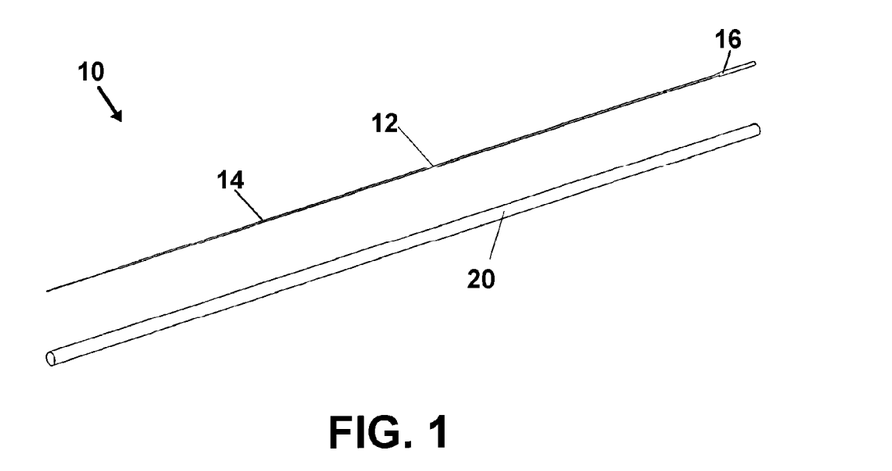
FIG. 1 shows a view of one preferred mode of the device employed to hold the sensing component and lead wire in operative electrical engagement using heat shrunk polymeric material such as a shrink wrap tube.

Now referring to drawings in FIGS. 1-16, wherein similar components are identified by like reference numerals, there is seen in FIG. 1 the sensor 12 and the heat shrinking or polymeric material shown as a shrink tube 20 which optionally may include an interior thermoplastic adhesive surface to provided increased adhesion of the formed polymeric jacket to the underlying assembly and/or catheter or wire. These components are employed in all particularly preferred modes of the medical sensor operative engagement and mounting system 10 herein. The assembled sensor 12 generally consists of an electrically conductive lead wire 14 and the sensing component 16 engaged thereon.

Again, the sensing component 16 can be any type of sensor or marker employed in the art of surgical navigation for example electromagnetic sensors which broadcast when provided electrical current from the lead wire 14 which forms the sensor assembly of an aggregate length of the two operationally and electrically engaged. Such sensors 12 are located within the body by electrical triangulation methods using known radiation patterns from the broadcasting sensor 12. Such sensor components 16 are formed of delicate windings and components which are of very small and fragile size, yet must be held in a reliable electrical communication with the guide wire 14 so as to provide the radiated broadcast patter required for the navigation system to operate.

Further, it is understood that for any type sensor component 16 employed, it is the object of the invention to provide a means to maintain a secure operative electrical connection between the sensing component 16 and the lead wire 14 without crimping, soldering, welding, or gluing, as noted herein. It is additionally noted and anticipated that although the sensor 12 is shown in its most simple form, depicting only the sensing component 16 and wire 14, it is within the scope of the invention, that in practice, the sensor 12 may employ a longer lead wire 14 or differently shaped sensing component 16 or additional sensing components and wires in the jacketed formation. As such those skilled in the art will appreciate the descriptions and depictions set forth in this disclosure or merely meant to portray examples of preferred modes within the overall scope and intent of the invention, and are not to be considered limiting in any manner.

Figure 2:
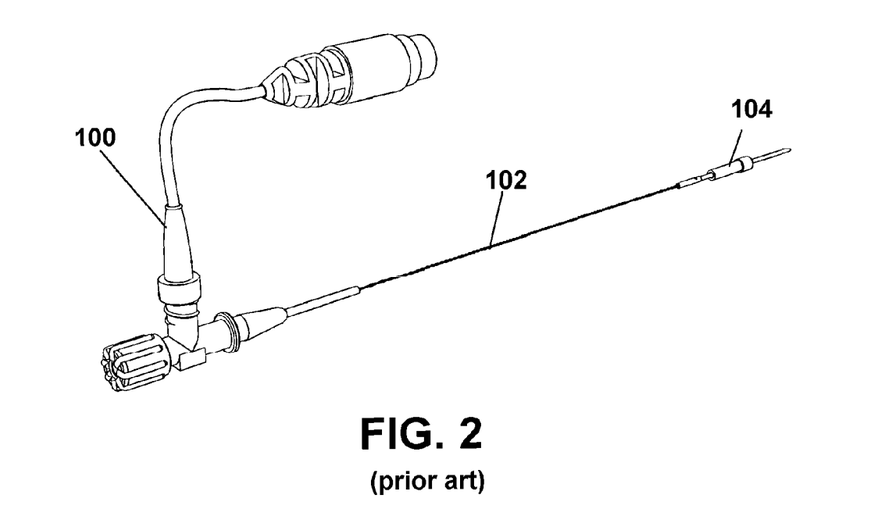
FIG. 2 depicts a prior art typical aspiration needle for use in combination with an operative lumen bearing device such as a catheter.

FIG. 2 shows a view of a typical conventional aspiration needle 100 as an example of one surgical instrument operated by a control wire within a lumen, to which the jacketed device 10 and method of engagement herein, is particularly well adapted. The following descriptions provide steps for the jacketed engagement of a lead wire 14 and sensing component 16 to form the operative the medical sensor 12. Additionally shown are modes of the device 10 where formed sensor 12 is operatively positioned adjacent to a control wire 102 using a concurrent or subsequent engagement of the assembled and jacketed sensor 12 to an elongated lumen-bearing device such as a catheter.

It must be noted that the steps described and components formed, can additionally be employed with other medical instruments using a control wire to operate an instrument at the distal end of a lumen, and is not to be considered limited to an aspiration needle which is depicted as an example.

Briefly, in this and other modes of the formed device 10, a jacket providing a movement-restricted insulated axial passage in which the sensing component 16 is held in operative electrical communication at the distal end of a control wire 14 is provided. This jacketed engagement yields the frictional and/or compressive force of a polymeric jacket which surrounds or is heat formed and adhered to the assembled sensing component 16 and lead wire 14. This novel means of maintaining a sensitive sensing component 16 to its required lead wire 14, is a significant advance over soldering, welding, and adhesives and the like previously used in that it results in virtually no failed components during manufacturing, thereby lowering costs.

Further, by the avoidance of mechanical engagement such as crimping, and soldering, and welding, the sensing component 16 is left in its designed condition physically, and the resulting sensor 12 has a sensing component 16 which radiates signals in its proper and designed radiation pattern, through the dialectic polymeric insulating layer which renders the sensor 12 fluid proof, which is also a requirement for proper operation thereof.

Using other modes of the basic structure of polymeric jacketing of the control wire 14 and sensing component 16 to form the sensor 12, may also be properly positioned upon a lumen-bearing housing such as a catheter 24 in an operative engagement thereto. Such an engagement provides operative positioning of the sensing component 16 to be employed with the navigation system and virtual-patient depiction during operative use of the device 10 herein. This operative engagement may be performed concurrently with the polymeric jacketing of the control wire 14 and sensing component 16 to form the sensor 12, or subsequent thereto depending on the formed structure.

In all modes the device 10 having the sensor 12 held in operative engagement by the polymeric jacketing, the components may be engaged with the catheter easily in a manner to place the sensing component properly positioned at or adjacent to, or extending from, the distal end 104 of the catheter and proximate to any surgical instrument being operated by the control wire. The sensor formation and mounting system 10 herein, will allow for higher quality lower cost operative sensors 12 thereby ensuring widespread use for physicians to track or otherwise follow the tips of there surgical instruments as needed for surgical navigation.

Figure 3:
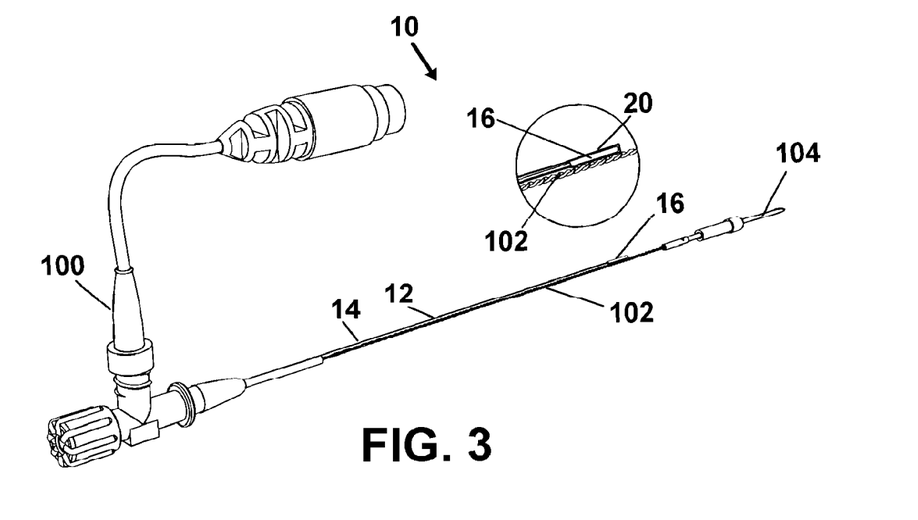
FIG. 3 shows a first step of one preferred mode of the employment of the device wherein the polymeric jacketed sensor is positional adjacent the control wire of the aspiration needle and insulated therefrom.

As shown in one mode, in the depiction and inset of FIG. 3, there is seen a preferred mode wherein the sensor 12, having been jacketed with polymeric material such as shrink tube 20, to operatively hold the sensing component 16 to the lead wire 14, is positioned to an engagement with a control wire 102 of the needle 100 or any wire-operated surgical instrument. The sensing component 16 may be operatively engaged to the control wire 102, at any position required for the operation of the engaged navigation system.

Of course this mode of engagement may have a narrow application in navigational surgery, but would easily be employable using the formation of sensor 12 and engagement herein described to form the structure of wire and wrapped sensor 12. In other modes employing the sensor 12 with other control-wire operated surgical instruments, for example biopsy forceps, the formed sensor 12 can be positioned at, extending from, or adjacent to the distal end of the catheter from which the surgical tool is deployed and operated. Because the sensor 12 is insulated by a formed polymeric jacket, the sensing component 16 is protected from moisture and if desired, can be positioned to project from the distal end of the catheter 24 adjacent to the surgical tool.

In FIG. 3, as can be seen the sensing component 16 is operatively positioned at or near the distal end 104 of a lumen operated surgical instrument such as a needle 100 with the lead wire 14 extending parallel along the length of the control wire 102. It is noted that the positioning of the sensor 12 along the instrument 100 can be of the designer's choice and should be considered limited by the depiction. Engagement to the lead control wire 102 however, does provide a means for navigation which will move with the instrument if desired. The polymeric jacket surrounding the assembled sensor 12 holds the component in a secure, flexible operative engagement allowing such an engagement and translation with the control wire.

Figure 4:
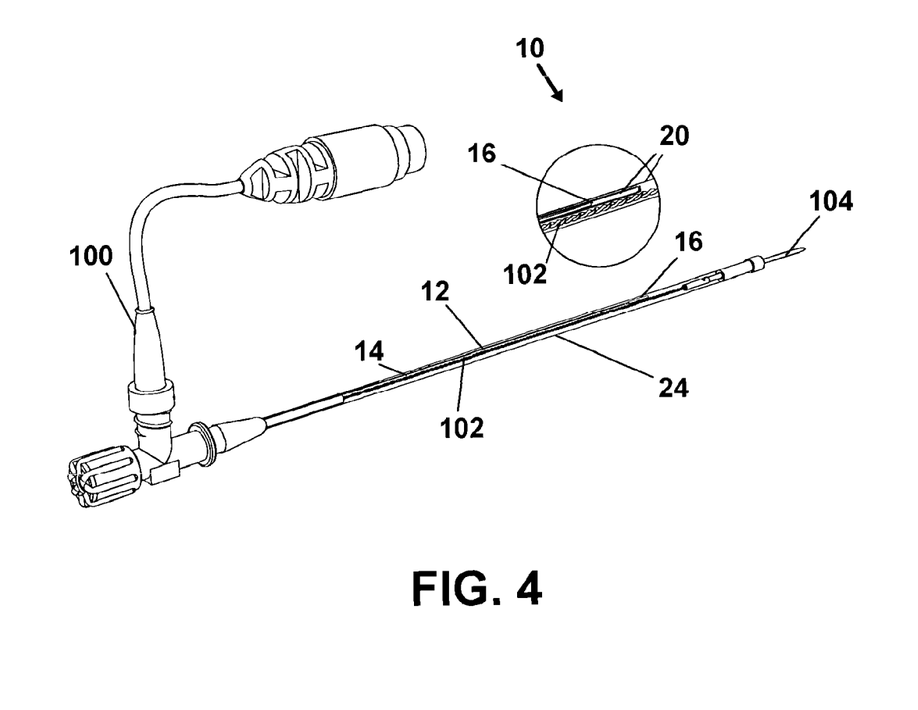
FIG. 4 shows a mode of the device of FIG. 3 showing the shrunken polymeric wrapped sensor, positioned within the lumen of a control wire providing one means to engage the formed and insulated sensor, with the catheter to be employed using the control wire operated instrument.

FIG. 4 shows a view depicting a next step wherein heat reactive polymeric material shown as the shrink tube 20 provides the means to hold the sensor 12 in a flexible translatable fashion, to the control wire 102. Upon application of heat, the compressive force of the polymeric material such as the shrink tube 20 upon the surface area of the elongated components, provides a means to securely engaged the sensor 12 to instrument control wire, as well as provide a means to maintain the fragile electrical connection between the lead wire 14 and sensing component 16 which may otherwise be damaged by conventional methods which would be potentially destroyed or rendered inoperative if engaged to and translated with the control wire around serpentine pathways of the body.

Figure 5:
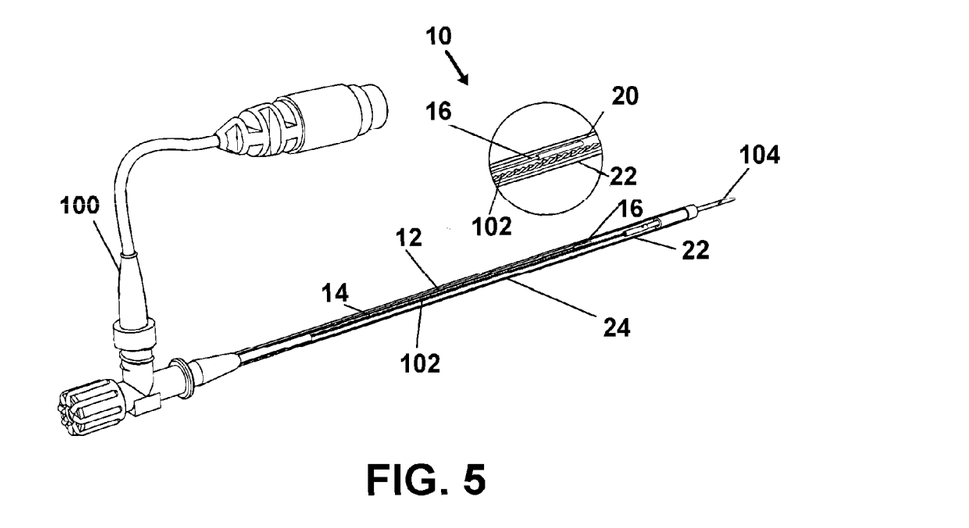
FIG. 5 shows another mode of sensor and tool engagement where polymeric jacket or other protective sleeve/tube is engaged over the shrink wrapped sensor and the control wire to engage the sensor directly to the control wire which will operate the surgical instrument.

FIG. 5 depicts the lumen-bearing catheter 24 engaged over the shrink tube 20, with the sensor 12 engaged to the control wire 102 by a polymeric jacket such as a second shrink tube 20. In other modes the shrink wrapped sensor 12 and control wire 102 can be protected by other protective means such as applying protective coatings, additionally layers of shrink tube, or other suitable means.

Figure 6:
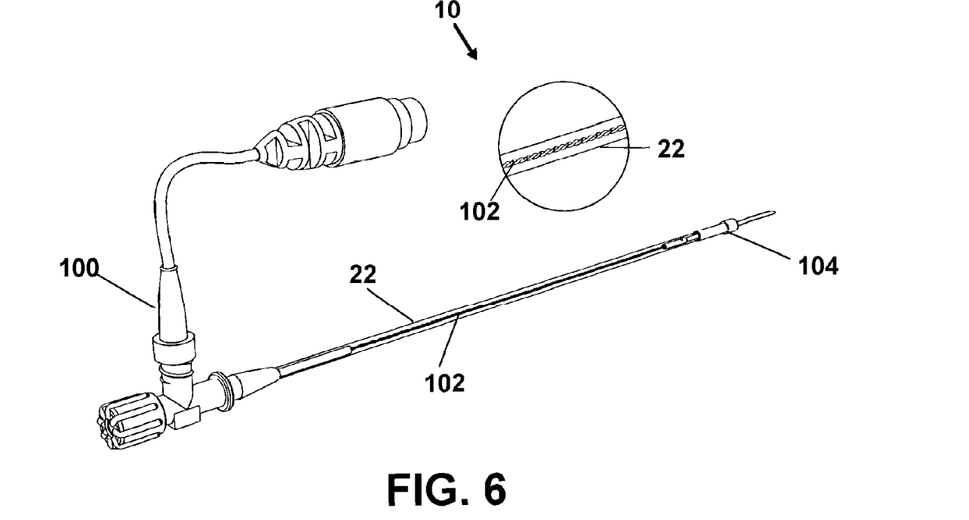
FIG. 6 depicts a first step of another particularly preferred mode of the device where a lumen for a catheter or other protective sleeve/tube is initially engaged over the control wire of a surgical tool such as an aspiration needle.

FIG. 6 depicts a mode of the device 10 wherein the formed sensor 12 is not directly in contact with the control wire 102 which would be desirable where the sensor 12 operates engaged to the catheter 24. As is shown in the depiction and inset, a first protective sleeve provided by the lumen of the catheter 24 is engaged over the control wire 102 in a translatable engagement within a lumen. This positions the control wire 102 isolated but immediately parallel and adjacent to the engagement of the sensor 12 to the catheter 24 or other lumen-bearing surgical component adapted to operate a control wire and the like.

Figure 7:
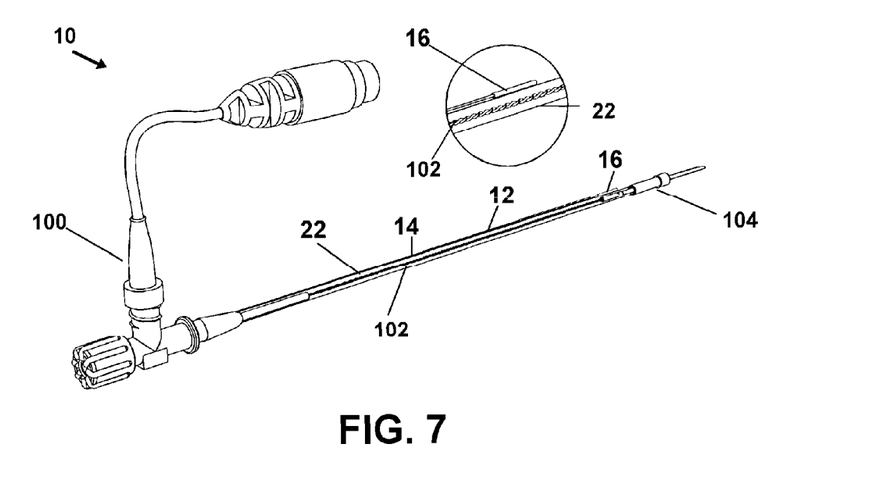
FIG. 7 shows a next step of the mode of the device of FIG. 6 wherein the sensor is positioned adjacent the formed protective jacket.

In FIG. 7 the sensor 12 is shown in engagement to the exterior surface of the protective catheter 24 sleeve 22 housing an internal lumen or lumens. Again it is generally desired to position the sensing component 16 in a registered position, at or adjacent to the distal end 104 of the catheter 24 engaged to the instrument 100 with the lead wire 14 extending parallel the length of the protective sleeve 22 or catheter 24.

Figure 8:
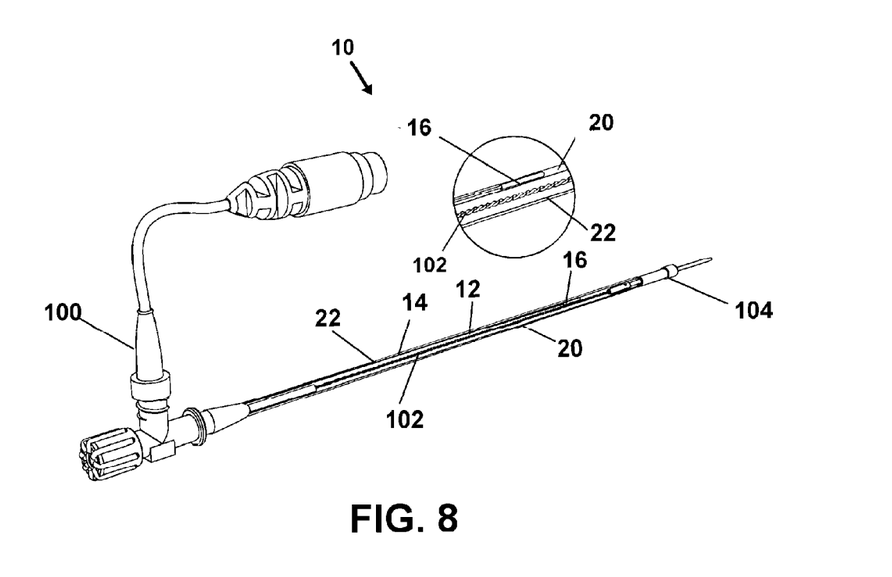
FIG. 8 depicts a next step in engaging the sensor to the lumen-bearing device such as a catheter showing a polymeric material or tube engaged over the sensor and catheter thereby providing means to securely engaged the formed sensor to the outer surface of the protective sleeve. This can be done concurrently as the means to hold the sensing component in electrical communication with the lead wire, or after such is done.

In FIG. 8, is shown the engagement of the sensor 12 to the exterior of the catheter 24 or sleeve 22 through the employment of heat shrinking polymeric material such as the depicted shrink tube 20. Using heat to retract the shrink tube 20 provides the polymeric jacket which is engaged over the formed sensor 12 and sleeve 22 or catheter 24. This engagement of the polymeric jacket or shrink tube 20 defines a liquid-protected, translation restrictive, insulated axial pathway for the sensor 12 between the exterior surface of the sleeve 22 or catheter 24, and the polymeric material forming the shrink tube 20.

The engagement of the polymeric material in this fashion may be done using sensor 12, which has already been operatively engaged with its own polymeric jacket from a shrink tube 20 or the like. Alternatively, this engagement mode of the polymeric jacket over the sensor 12 and sleeve 22 or catheter 24, may in a single step, be employed to securely engaged the sensor 12 to the outer surface of the sleeve 20 or catheter 24, as well as provide a compressive polymeric jacket to maintain the fragile electrical connection between the lead wire 14 and sensing component 16 which may otherwise be damaged by conventional methods. It must be noted that an additional step (not shown) may be employed if desired, wherein another protective element is engaged over the shrink tube 22.

Figure 9:
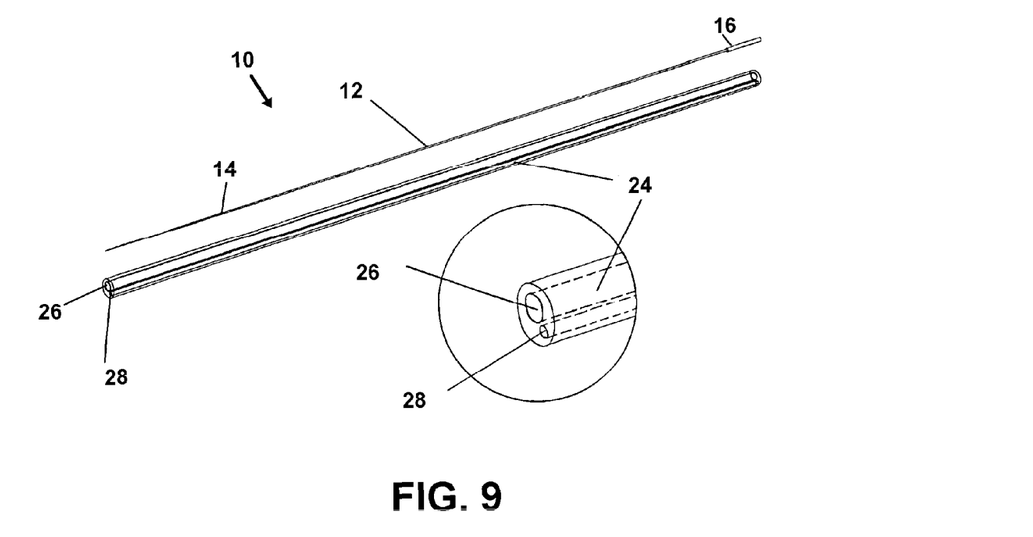
FIG. 9 shows a view of the preferred sensor and double lumen catheter component in accordance with at least one other particularly preferred mode of the device, ready for assembly.

There is seen in FIG. 9, another view of the sensor 12 and catheter 24 components which are employed in another particularly preferred mode of the device 10. In this mode the catheter 24 is preferably at least a double lumen catheter 24 having one lumen 26 configured for translation of a control wire, and a second lumen 28 sized to yield the polymeric jacket frictionally engaged the exterior of the lead wire 14 and sensing component 16. Of course those skilled in the art will realize that the size of the diameters are relative the medical instrument and sensor 12 to be employed.

Figure 10:
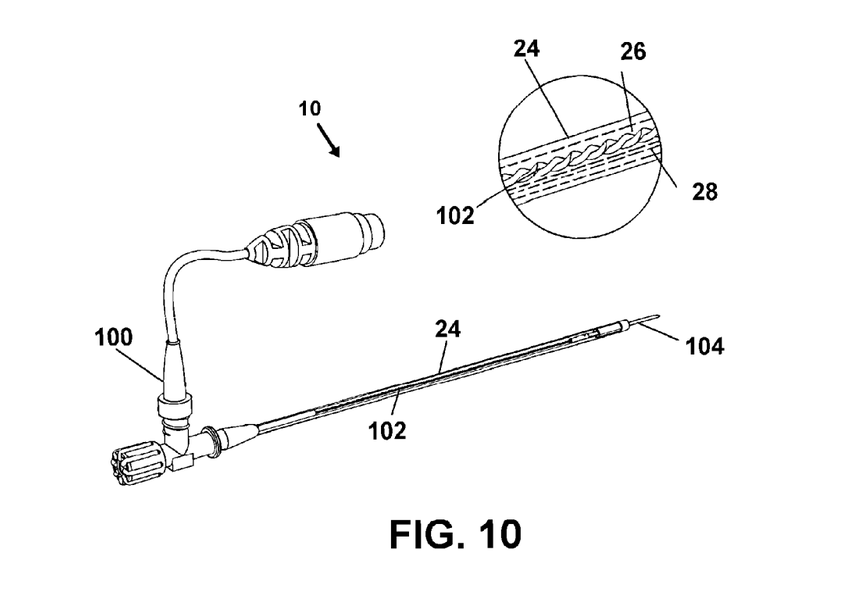
FIG. 10 shows the positioning of the sensor device within one lumen of a double lumen catheter wherein the control wire of the aspiration needle may be engaged within the other of the two lumen.

In FIG. 10 the device in FIG. 9 is shown wherein the control wire 102 is engaged within the first lumen 26 and the sensor 12 is engaged within the second lumen 28. In this mode, the sensor 12 may be previously assembled using the aforementioned polymeric jacket of heat shrink material to hold the sensing component 16 operatively to the lead wire 14, or the second lumen 28 itself can provide the holding function for the components of the sensor 12 through formation of the diameter and length of the second lumen to maintain the sensor 12 tightly held to the lead wire.

Figure 11:
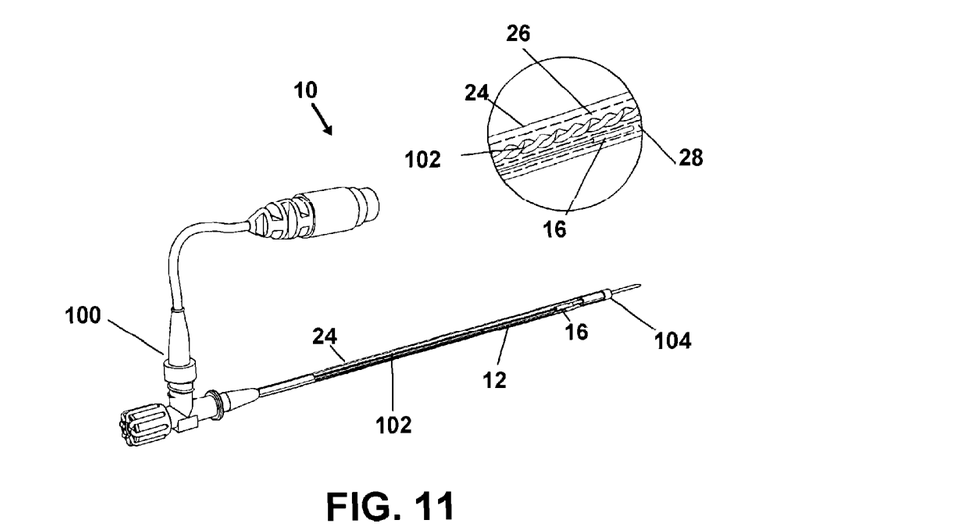
FIG. 11 shows the device of FIG. 10 wherein the sensor is operationally engaged within a lumen adapted in size to hold the sensor in operational engagement in an insulated axial passage for the sensor components which is parallel to the lumen for the control wire.

If the second lumen 28 is to be employed for the jacket to operatively engage the sensing component 16 to the lead wire 14, it is sized to define a translation-restrictive insulated axial pathway, preferably equal to, or slightly shorter than the aggregate length of the assembled lead wire 14 and sensing component 16. In this manner the sensing component 16 is held firmly electrically engaged to the lead wire 14 by the second lumen 28 pathway. In this case thermoplastic adhesive may or may not be employed since the second lumen is sized to hold the assembly in operative engagement.

To that end, the second lumen 28 is sized or otherwise formed to diameter and length, to exert a biased compressive force on the sensing component 16 against and on the lead wire 14 to form the operative sensor 12, when in the engaged position within the lumen. This will provide a means to maintain a secure electrical connection between the lead wire 14 and sensing component 16 in manner that does not damage it. To hold the sensing component 16 against and biased onto the lead wire 14, the distal end of the second lumen 28, is totally blocked which concurrently provides a fluid sealed axial cavity. The lead wire 14 extends to the proximate end of the second lumen 28, through a block, which forms a length of the second lumen equal to, or slightly smaller than the length of the combined sensing component 16 assembled to the lead wire 14. This causes a slight pushing or bias on the distal end block against the sensing component 16 during use, holding it in operative electrical engagement on the lead wire 14.

Figures 12, 12A:
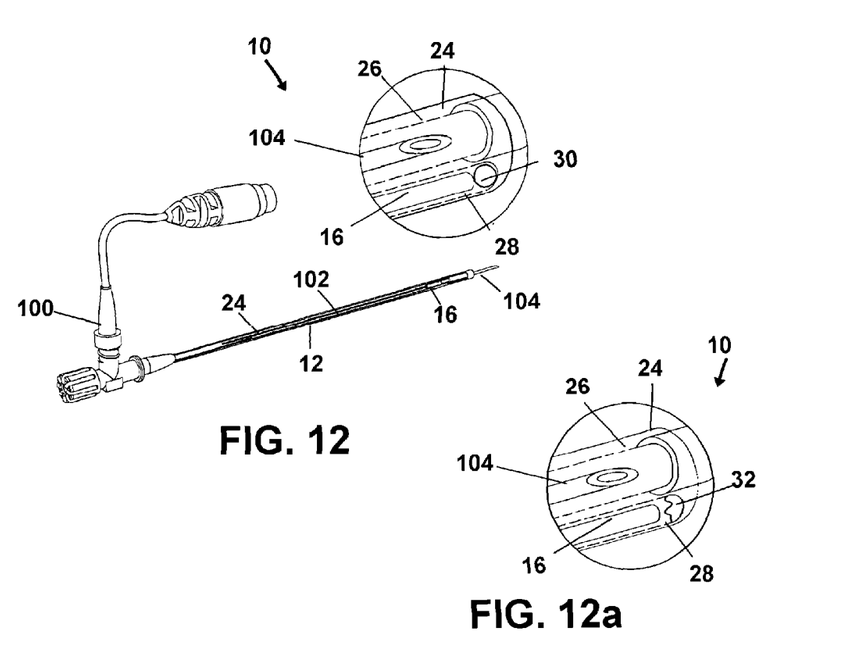
FIG. 12 depicts the distal end of the sensor-occupied lumen sealed closed through the provision of medical adhesive, heated polymeric material, and or thermoplastic adhesive as noted, or other means for sealing thereby providing a dry insulated positioning adjacent to the control wire.
FIG. 12a depicts a mode of sealing the distal end of the sensor-occupied lumen, wherein the distal end of the sensor engaged lumen is sealed via ultrasonic welding.

FIG. 12 and FIG. 12a shows views of the described configuration showing the distal end of the second lumen 28 adjacent the sensing component 16 and sealed or otherwise capped with seals on both a proximal and distal end, to provide additional insulation and protection to the sensor 12 and a bias of the end of the sensing component 16 toward the end of the lead wire 14. The end can seals may be formed with medical adhesives 30, ultrasonic welding 32, or other means suitable for the intended purpose. The distance between the two seals within the second lumen 28 would define the total length of the second lumen 28 which is preferably equal to or slightly less than the aggregate length of the sensor assembly formed of sensing component 16 and lead wire 14. This would provide the biasing force noted earlier to hold the sensing component 16 operatively electrically engaged on the lead wire 14.

Figure 13:
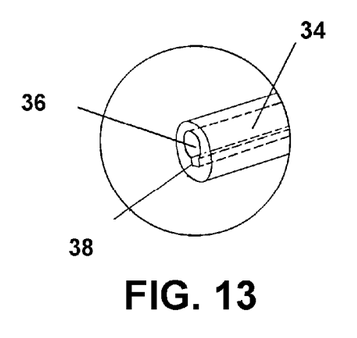
FIG. 13 shows a catheter which can be employed in yet another preferred mode of the device wherein the assembled and polymeric-insulated sensor is engageable within an interior longitudinal groove, spaced from but parallel and proximate to, the adjacent the axial passage of the lumen.

FIG. 13 shows another favored mode of assembly and engagement of the sensor 12 to single lumen catheter 34 which can be employed in another particularly preferred mode of the invention. As can be seen the catheter 34 includes a single lumen 36 having at least one longitudinally extending groove, cavity, or pathway 38 communicating within the interior of the catheter 34 adjacent the lumen 36. One skilled in the art will immediately recognize that employment of the catheter 34 involves communicating the control wire 102 within the lumen 36 and similarly engaging the sensor 12 within the groove 38 in a position adjacent the control wire 102. The groove 38 will be sufficiently deep to avoid translational contact of the sensor 12 with the control wire and the sensor can be preassembled with the polymeric jacket formed by shrinking of the tube 20 or the like, or, the lead wire 14 and sensing component 16 may be placed in the groove which will be sized to hold them in electrical operative engagement, and the portion of the groove communicating with the lumen 36 will be sealed with adhesive, or polymeric material to insulate the formed sensor 12 from the control wire. Depending on the material forming the tube 20, thermoplastic adhesive on the interior of the tube 20 may or may not be employed. In some instances, heating the tube 20 to substantially melting temperature will sever to bond it to the material forming the catheter having the lumen 36. In others, thermoplastic adhesive may be desired to enhance engagement and can be employed. Some types of heat shrink contain a layer of thermoplastic adhesive on the inside to help provide a good seal and better adhesion, while others rely on friction from the closely conforming materials. Heating plain, non-adhesive shrink tube to very near the melting point may allow it to fuse to the underlying material as well. This would be the case whenever the tube 20 is engaged to the lumen-bearing device such as a catheter.

Figure 14:
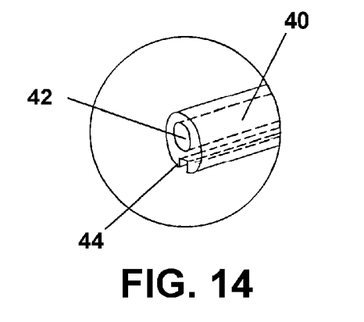
FIG. 14 shows another particularly preferred mode of the device using an engagement to catheter. In this mode the assembled sensor may be engaged in a longitudinal groove, or held assembled within the groove, with a subsequent engagement of adhesive or shrinking polymeric material thereover.

FIG. 14 shows another mode of the device herein where a catheter 40 which can be employed with yet another particularly preferred mode formation and or mounting of the formed sensor 12 of the invention. As can be seen the catheter 40 includes a single lumen 42 although it may have more. The lumen 42 has at least one longitudinally extending groove, cavity, or pathway 44 communicating into the exterior surface of the catheter 40. One skilled in the art will immediately recognize that employment of the catheter 40 involves communicating the control wire 102 within the lumen 42. Further, in a manner similar to that described in FIG. 13, the sensor 12 may be preformed with its polymeric jacket and lain within the groove 44 in a position adjacent the control wire 102. Alternatively, the control wire 14 and the sensing component 16 may be placed and held in operative electrical engagement by the compressive force of the groove 44 cut to provide such. Thereafter, the groove 44 may be filled with polymeric material, or adhesive, or polymeric material in the form of a shrink tube 20 (not shown) may be heated to compressively engage the recessed sensor 12 in order to insure secured engagement within the exterior groove 44.

Figures 15, 16:
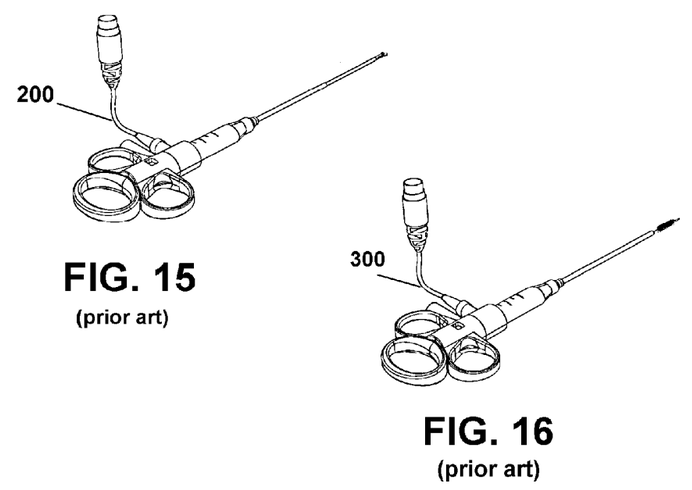
FIG. 15 depicts conventional biopsy forceps which is shown as an example of one of the many catheter operated surgical instruments to which any of the disclosed modes of the device may be employed.
FIG. 16 depicts another conventional catheter type surgical instrument to which any mode of the device herein may be employed in the form of cytology brush, and to show that any surgical instrument operated with a control wire through a lumen, can have any mode of the device herein employed therewith.

FIG. 15 and FIG. 16 show examples of other conventional medical instruments, employing catheters and control wires such as biopsy forceps 200 and a cytology brush 300 respectively, which would benefit from the present invention. These conventional instruments are also shown to depict the fact that the device and invention herein, is employable with any surgical instrument employing a tube having a catheter to operate a control wire for a surgical instrument that is to be electronically tracked, and such is anticipated within the scope of this invention.

Those skilled in the art will recognize that slight modifications to the previously disclosed steps for employing any of the preferred modes of the invention may be required in order to properly employ the device with these and other instrument, and are anticipated.

While all of the fundamental characteristics and features of the invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. An engagement system of a surgical sensor assembly, formed of a sensing component in a fixed position upon, and communicating with, a lead wire, said engagement system comprising:
   a jacket of polymeric material;
   said jacket being formed by a first lumen of a multi-lumen catheter;
   said first lumen having a first seal at a distal end and a second seal at a proximal end of said catheter;
   a distance between said first seal and said second seal thereby defining a distance of said first lumen;
   said distance being equal to or slightly less than an aggregate length of said surgical sensor assembly formed by an said sensing component in operative electrical engagement to said lead wire;
   contact of said sensing component and said lead wire with said first and said second seals, providing a biasing force upon said sensing component, said biasing holding said sensing component in said operative electrical engagement to said lead wire; and
   said jacket positioned to surround both said lead wire and said sensing component for an aggregate length of said assembly formed of said sensing component operatively engaged to said lead wire, whereby said sensing component is held in operative electrical engagement to said lead wire by a contact between said jacket and respective exterior surfaces of said sensing component and said lead wire.

2. The engagement system of claim 1, additionally comprising:
   said surgical sensor assembly being employed in combination with a catheter having at least one lumen therein for translation and operation of a control wire for a surgical instrument; and
   a second said jacket of polymeric material, said second jacket engaging said surgical sensor assembly to said lead wire.

3. The engagement system of claim 1, additionally comprising:
   said jacket of polymeric material being formed of heat-shrink tubing;
   said heat-shrink tubing having an interior surface having thermoplastic adhesive thereon;
   said interior surface of said heat-shrink tubing providing said contact between said jacket and respective exterior surfaces of said sensing component and said lead wire; and
   said contact being compressive and adhesive against said exterior surfaces.

4. The engagement system of claim 3, additionally comprising:
   said surgical sensor assembly being employed in combination with a catheter having at least one lumen therein for translation and operation of a control wire for a surgical instrument; and
   a second said jacket of polymeric material, said second jacket engaging said surgical sensor assembly to said lead wire.

5. The engagement system of claim 3, additionally comprising:
   said surgical sensor assembly being employed in combination with a catheter having at least one lumen therein for translation and operation of a control wire for a surgical instrument;
   a recess formed in an exterior surface of said catheter parallel to said lumen;
   said surgical sensor assembly positioned within said recess; and
   a second said jacket of polymeric material formed of said heat-shrink tubing, said second jacket surrounding said exterior surface of said catheter and providing means to maintain said surgical sensor assembly positioned therein.

6. The engagement system of claim 1, additionally comprising:
   said jacket of polymeric material being formed of heat-shrink tubing, said heat shrink tubing providing said contact between said jacket and respective exterior surfaces of said sensing component and said lead wire; and
   said contact being compressive against said exterior surfaces.

7. The engagement system of claim 6, additionally comprising:
   said surgical sensor assembly being employed in combination with a catheter having at least one lumen therein for translation and operation of a control wire for a surgical instrument; and
   a second said jacket of polymeric material, said second jacket engaging said surgical sensor assembly to said lead wire.

8. The engagement system of claim 6, additionally comprising:
   said surgical sensor assembly being employed in combination with a catheter having at least one lumen therein for translation and operation of a control wire for a surgical instrument;
   a recess formed in an exterior surface of said catheter parallel to said lumen;
   said surgical sensor assembly positioned within said recess; and
   a second said jacket of polymeric material formed of said heat-shrink tubing, said second jacket surrounding said exterior surface of said catheter and providing means to maintain said surgical sensor assembly positioned therein.

9. The engagement system of claim 6, additionally comprising:
   said surgical sensor assembly being employed in combination with a catheter having an interior surface wall defining at least one lumen therein for translation and operation of a control wire for a surgical instrument;
   a recess formed in said surface wall; and
   said surgical sensor assembly positioned within said recess;
   an insulating layer positioned between said surgical sensor assembly and said control wire.

10. The engagement system of claim 1, additionally comprising:
    said polymeric material being one or a combination of polymeric materials which shrink when heated to form said contact, from a group of polymeric materials including, polyester, polyolefin, flouropolymers, polyurethane, polyvinyl chloride and polyester, polyethylene terephthalate, PVC, neoprene, and silicone elastomer.

11. The engagement system of claim 10, additionally comprising:
    said surgical sensor assembly being employed in combination with a catheter having an interior surface wall defining at least one lumen therein for translation and operation of a control wire for a surgical instrument;
    a recess formed in said surface wall; and said surgical sensor assembly positioned within said recess;

an insulating layer positioned between said surgical sensor assembly and said control wire.

12. The engagement system of claim 2, additionally comprising:
said jacket of polymeric material being formed of heat-shrink tubing, said heat shrink tubing providing said contact between said jacket and respective exterior surfaces of said sensing component and said lead wire; and
said contact being compressive against said exterior surfaces, said compressive force being determined by said material employed.

13. The engagement system of claim 12, additionally comprising:
said surgical sensor assembly being employed in combination with a catheter having at least one lumen therein for translation and operation of a control wire for a surgical instrument; and
a second said jacket of polymeric material, said second jacket engaging said surgical sensor assembly to said lead wire.

14. The engagement system of claim 12, additionally comprising:
said surgical sensor assembly being employed in combination with a catheter having at least one lumen therein for translation and operation of a control wire for a surgical instrument;
a recess formed in an exterior surface of said catheter parallel to said lumen;
said surgical sensor assembly positioned within said recess; and
a second said jacket of polymeric material formed of said heat-shrink tubing, said second jacket surrounding said exterior surface of said catheter and providing means to maintain said surgical sensor assembly positioned therein.

15. The engagement system of claim 10, additionally comprising:
said jacket of polymeric material being formed of heat-shrink tubing;
said heat-shrink tubing having an interior surface having thermoplastic adhesive thereon;
said interior surface of said heat-shrink tubing providing said contact between said jacket and respective exterior surfaces of said sensing component and said lead wire; and
said contact being compressive and adhesive against said exterior surfaces.

16. The engagement system of claim 15, additionally comprising:
said surgical sensor assembly being employed in combination with a catheter having at least one lumen therein for translation and operation of a control wire for a surgical instrument;
a second said jacket of polymeric material, said second jacket engaging said surgical sensor assembly to said lead wire.

17. The engagement system of claim 15, additionally comprising:
said surgical sensor assembly being employed in combination with a catheter having at least one lumen therein for translation and operation of a control wire for a surgical instrument;
a recess formed in an exterior surface of said catheter parallel to said lumen;
said surgical sensor assembly positioned within said recess; and
a second said jacket of polymeric material formed of said heat-shrink tubing, said second jacket surrounding said exterior surface of said catheter and providing means to maintain said surgical sensor assembly positioned therein.

18. An engagement system of a surgical sensor assembly, formed of a sensing component in a fixed position upon, and communicating with, a lead wire, said engagement system comprising:
a jacket of polymeric material, said jacket positioned to surround both said lead wire and said sensing component for an aggregate length of said assembly formed of said sensing component operatively engaged to said lead wire, whereby said sensing component is held in operative electrical engagement to said lead wire by a contact between said jacket and respective exterior surfaces of said sensing component and said lead wire;
said surgical sensor assembly being employed in combination with a catheter having at least one lumen therein for translation and operation of a control wire for a surgical instrument;
a recess formed in an exterior surface of said catheter parallel to said lumen;
said surgical sensor assembly positioned within said recess; and
a second said jacket of polymeric material formed of said heat-shrink tubing, said second jacket surrounding said exterior surface of said catheter and providing means to maintain said surgical sensor assembly positioned therein.

19. An engagement system of a surgical sensor assembly, formed of a sensing component in a fixed position upon, and communicating with, a lead wire, said engagement system comprising:
a jacket of polymeric material, said jacket positioned to surround both said lead wire and said sensing component for an aggregate length of said assembly formed of said sensing component operatively engaged to said lead wire, whereby said sensing component is held in operative electrical engagement to said lead wire by a contact between said jacket and respective exterior surfaces of said sensing component and said lead wire;
said surgical sensor assembly being employed in combination with a catheter having an interior surface wall defining at least one lumen therein for translation and operation of a control wire for a surgical instrument;
a recess formed in said surface wall; and
said surgical sensor assembly positioned within said recess;
an insulating layer positioned between said surgical sensor assembly and said control wire.

* * * * *